US00PP08819P

United States Patent [19]

Button et al.

[11] Patent Number: Plant 8,819

[45] Date of Patent: Jul. 5, 1994

[54] ANTHURIUM PLANT NAMED COTTON CANDY

[75] Inventors: Richard J. Button, 1245 Obisbo Ave., Coral Gables, Fla. 33134; Ann E. Lamb, Lake Placid, Fla.

[73] Assignee: Richard J. Button, Coral Gables, Fla.

[21] Appl. No.: 102,236

[22] Filed: Aug. 5, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named Cotton Candy characterized by its cupped pink flowers which are held above the foliage, dense compact habit, abundant branches, and leathery, dark green, triangular, shiny leaves.

1 Drawing Sheet

The present invention comprises a new and distinct cultivar of Anthurium, botanically known as *Anthurium hybrid,* and referred to by the cultivar name Cotton Candy.

The new cultivar is a product of a planned breeding program carried out in Miami, Fla. by co-inventor Richard J. Button. The seedling is a result of a cross of unknown parentage made in Miami, Fla. The cultivar was discovered from the progeny of the stated cross in Palmdale, Fla. by co-inventor Ann E. Lamb. Asexual propagation by tissue culture by co-inventor Ann E. Lamb in Palmdale, Fla. increased the number of plants for evaluation and clearly demonstrated the stability of the combination of characteristics of Cotton Candy from generation to generation.

The following observations, measurements and values describe plants grown in Apopka, Fla. under greenhouse conditions which closely approximate those generally used in horticultural practice.

The following traits have been repeatedly observed to be characteristics which in combination distinguish Cotton Candy from other Anthuriums of the same general type, for example, the well known cultivar Lady Jane.

1. The plant produces distinctly cupped pink flowers which gradually fade to green.
2. The flowers are held upright above and among the foliage.
3. The distinctly triangular leaves are leathery, dark green, durable, and have a shiny surface.
4. The plant habit is dense and compact.
5. The plant is free branching.

All color references are to the Royal Horticultural Society (RHS) Colour Chart. Colors may vary slightly depending on horticultural practices such as light level and fertilization rate, among others, without, however any change in genotype.

The color photographic drawing comprises a top perspective view of the inflorescence and foliage of a plant of Cotton Candy in a 15.5 cm pot. The photograph was taken approximately 40 weeks after planting a 20 week old liner obtained by tissue culture and grown under appropriate growing conditions. Colors are as accurate as possible with color illustrations of this type.

Origin: Seedling of unknown parentage.

Classification: *Anthurium hybrid,* cv, Cotton Candy.

Propagation: Asexual production either by tissue culture or division.

Plant: When a 20 week old liner is grown in a 15.5 cm pot for 40 weeks under appropriate growing conditions, Cotton Candy reaches a mature size of approximately 28 cm. to 32 cm. in height and approximately 35 cm to 40 cm. in width.

Leaves:

*Form.*—The leaf blade is deltoid with a cuspidate tip and a truncate base. The margins are entire. The midrib is straight over the length of the leaf. The leaf blade tends to be flat over the width of the leaf. The leaf margin is slightly wavy.

*Size.*—Leaf blades of a mature sized plant are approximately 15.5 cm to 18 cm in length and 11 cm to 12.5 cm in width.

*Petiole.*—The petiole is approximately 15 cm to 17.3 cm in height from the base of the petiole to the base of the leaf blade on the primary shoot. Secondary shoots are somewhat smaller depending on the age of the shoot. The petiole is approximately 4.0 mm in diameter just below the geniculum, and straight.

*Petiole wings.*—Petiole wings are approximately 1.4 cm to 1.7 cm in length and approximately 4.5 mm in width at their midpoint. The tips of the petiole wings are cordate. There is approximately 12.5 cm to 16.5 cm between the top of the wing and the base of the geniculum.

*Geniculum.*—The geniculum is approximately 22 mm to 25 mm in length, approximately 5 mm in diameter, and is often curved. The color is 146B. There is no space between the top of the geniculum and the base of the leaf blade. The geniculum is prominent.

*Veins.*—Veins are sunken, with the leaf blade slightly convex or flat between veins on the upper surface. The midrib protrudes from the upper surface of the leaf for approximately ⅔ the length of the leaf. Well defined primary veins on leaves radiate out from the juncture of the petiole and the leaf. Veins stand out prominently on the lower side. There are approximately 4–6 primary veins on the leaf.

*Lobes.*—The leaf has two rounded lobes which do not extend past the petiole. The distance from the petiole/leaf juncture to the highest point on the lobes is approximately 7.0 cm to 8.1 cm.

*Color.*—Upper surface: Closest to 139A but considerably darker. Lower surface: 146B. Midrib, upper surface: 137C. Midrib, lower surface: 146B. Petiole: 146B. Petiole wing: 146B-C.

INFLORESCENCE

Immature spathe: The spathe is tightly rolled around the spadix and extrudes from the petiole sheath. The spathe is substantially fully open when the pedicel is fully elongated, approximately 29 cm to 37 cm above the soil surface.

Mature spathe:

*Size.*—The flattened spathe is approximately 5.3 cm to 5.7 cm long and 5 cm to 5.2 cm in width.

*Color.*—Fully open: Upper surface: Between 48A-B and 50C. Lower surface: Closest to, but pinker than 48C. Faded: Upper surface: 144B with a pink cast. Lower surface: 144A with a pink cast.

*Arrangement.*—The spathe stands up on straight wiry pedicels and opens vertically above the leaves.

*Shape.*—The spathe is ovate with a cordate base and a cuspidate apice that is slightly hooked. It is distinctly cupped when first open and is approximately 5.2 cm to 5.5 cm in height, 4.5 cm to 4.8 cm in width, are approximately 1.0 cm in depth. The spathe remains cupped as it ages.

*Flowering time.*—After approximately 10 months from a 20 week old liner for an untreated plant as illustrated in the photograph, and depending on season, approximately 4 to 6 blossoms will be present. Smaller blossoms may occur on less mature growth. First flowers (1 to 3) can be expected approximately 4–5 months after planting a 20 week old liner.

REPRODUCTIVE ORGANS

Spadix:

*Size.*—Approximately 3.4 cm to 3.7 cm in height and 6 mm in width.

*Color.*—When the spathe unrolls, the spadix is 33C at the tip, blending to 47D, then to 75D for approximately one-half the length of the spadix. The spadix gradually changes to lighter than 146D before senescing.

*Stamens.*—Anthers and filaments are not clearly visible.

*Pollen.*—158D in color.

*Pistils.*—Lighter than 19D in color, protruding between the staminate flowers, firmly fixed to the main axil. The pistilate flowers extend approximately 0.2 mm beyond the staminate flowers.

Roots: White fleshy roots with fine laterals.

GENERAL OBSERVATIONS

Anthurium Cotton Candy has distinct cupped pink flowers which gradually fade to green. The flowers are held upright, above and among the foliage. The leaves are distinctly triangular in shape, leathery, dark green, shiny and durable. The plant habit is dense, branched, and compact. These combined characteristics make Cotton Candy a unique new cultivar.

What is claimed is:

1. A new and distinct cultivar of Anthurium plant named Cotton Candy, as illustrated and described.

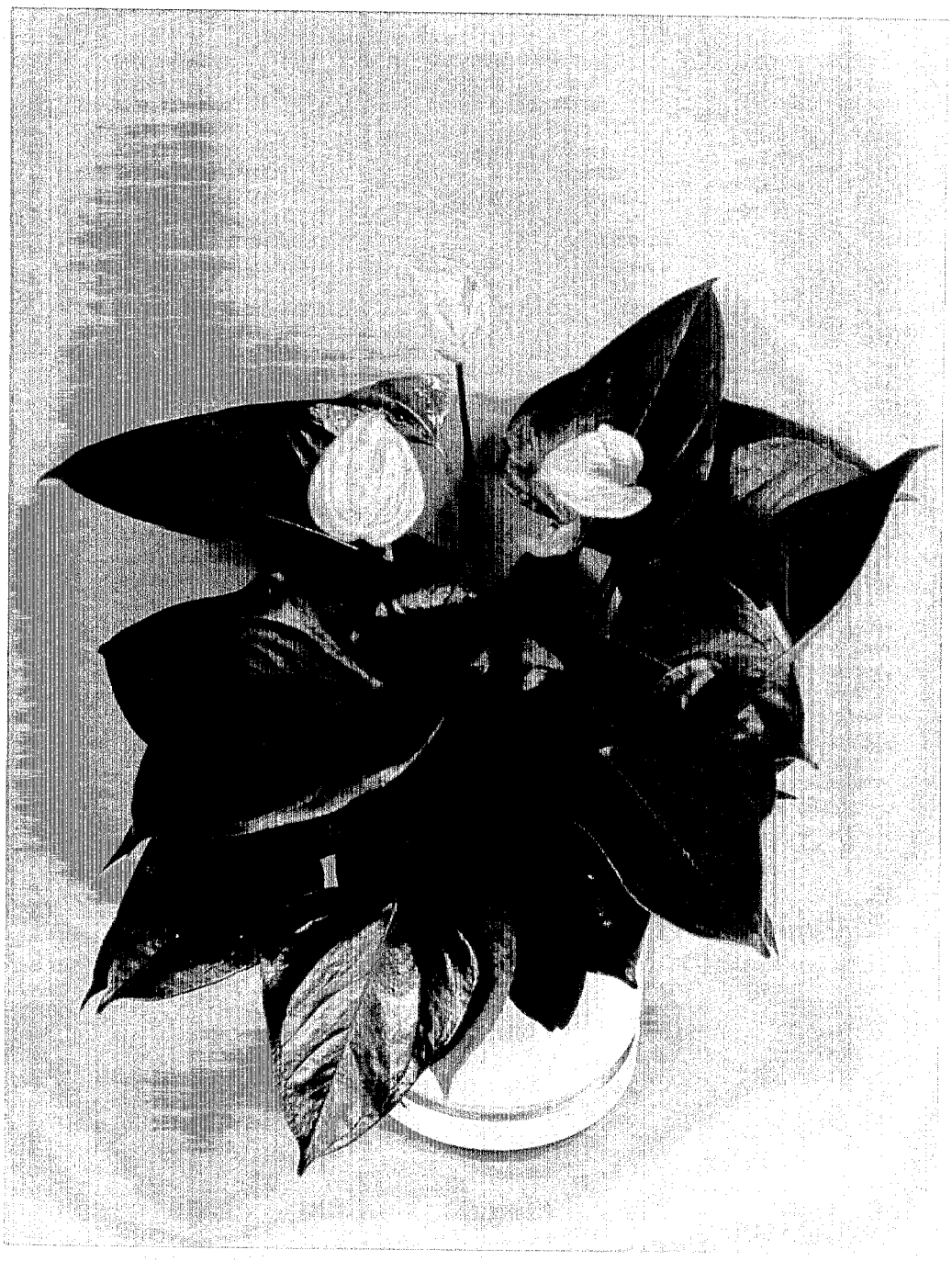

* * * * *